(12) United States Patent
Lee et al.

(10) Patent No.: US 11,446,347 B2
(45) Date of Patent: Sep. 20, 2022

(54) **ANTITHROMBOTIC COMPOSITION COMPRISING *ANGELICA GIGAS* NAKAI EXTRACT**

(71) Applicant: Astrogenesis Co., Ltd., Seoul (KR)

(72) Inventors: Kang Hyun Lee, Seoul (KR); Min Kuk, Seoul (KR)

(73) Assignee: ASTROGENESIS CO., LTD., Seoul (KR)

( * ) Notice: Subject to any disclaimer, the term of this patent is extended or adjusted under 35 U.S.C. 154(b) by 0 days.

(21) Appl. No.: 17/052,856

(22) PCT Filed: May 13, 2019

(86) PCT No.: PCT/KR2019/006004
§ 371 (c)(1),
(2) Date: Nov. 4, 2020

(87) PCT Pub. No.: WO2019/221571
PCT Pub. Date: Nov. 21, 2019

(65) Prior Publication Data
US 2021/0228665 A1 Jul. 29, 2021

(30) Foreign Application Priority Data

May 14, 2018 (KR) ........................ 10-2018-0054976

(51) Int. Cl.
| | | |
|---|---|---|
| *A61K 36/00* | (2006.01) | |
| *A61K 36/232* | (2006.01) | |
| *A23L 29/00* | (2016.01) | |
| *A23L 33/00* | (2016.01) | |
| *A23L 33/105* | (2016.01) | |
| *A61P 7/02* | (2006.01) | |
| *A61P 1/00* | (2006.01) | |
| *A61K 9/00* | (2006.01) | |
| *A61K 31/352* | (2006.01) | |
| *A61K 31/575* | (2006.01) | |
| *A61K 31/7048* | (2006.01) | |
| *A61K 45/06* | (2006.01) | |

(52) U.S. Cl.
CPC .......... *A61K 36/232* (2013.01); *A23L 29/035* (2016.08); *A23L 33/105* (2016.08); *A23L 33/30* (2016.08); *A61K 9/0053* (2013.01); *A61K 31/352* (2013.01); *A61K 31/575* (2013.01); *A61K 31/7048* (2013.01); *A61K 45/06* (2013.01); *A61P 1/00* (2018.01); *A61P 7/02* (2018.01); *A61K 2236/33* (2013.01)

(58) Field of Classification Search
CPC ....................................................... A61P 7/02
See application file for complete search history.

(56) References Cited

FOREIGN PATENT DOCUMENTS

| | | |
|---|---|---|
| CN | 104435027 | 3/2015 |
| KR | 10-0784339 | 12/2007 |
| KR | 10-2010-0047544 | 5/2010 |
| KR | 10-2014-0017741 | 2/2014 |
| KR | 101404168 B1 * | 6/2014 |
| KR | 101404168 B1 * | 6/2014 |
| KR | 10-2015-0118773 | 10/2015 |
| KR | 10-2017-0091535 | 8/2017 |
| KR | 20170091535 A * | 8/2017 |
| KR | 10-2018-0016275 | 2/2018 |
| KR | 10-1824970 | 2/2018 |
| KR | 10-2018-0042035 | 4/2018 |
| WO | 2020-071620 | 4/2020 |

OTHER PUBLICATIONS

Sa-Rang Oh et al., "Protective effect of decursin and decursinol angelate-rich Angelica gigas Nakai extract on dextran sulfate sodium-induced murine ulcerative colitis", Asian Pacific Journal of Tropical Medicine 10(9) (2017), 864-870, Sep. 2017.
Sook-Jin Kim et al., "Simultaneous Determination of Decursin, Decursinol Angelate, Nodakenin, and Decursinol of Angelica gigas Nakai in Human Plasma by UHPLC-MS/MS: Application to Pharmacokinetic Study", Molecules 23, 1019, Apr. 2018.
Pia LoretoWerlinger Bravo et al., "Antithrombotic Effect of the Ethanol Extract of Angelica gigas Nakai (AGE 232)", Life 2021, 11(9), 939, Sep. 2021.
JPO, Office Action of the corresponding Japanese Patent Application No. 2021-514270 dated Nov. 9, 2021.
KIPO, A PCT Search Report & Written Opinion of PCT/KR2019/006004 dated Sep. 10, 2019.
Min Yeong Kim et al., "The Effect of Angelicae gigantis radix according to Heat-process on Anti-Oxidant and Anti-Thrombotic", Kor. J. Herbol. 2016 31(3) : 13-22. http://dx.doi.org/10.6116/kjh.2016.31.3.13.
Seong-Soo Choi et al., "Effect of Decursinol on the Aspirin-induced Gastric Ulcer in Mice", J Korean Soc Appl Biol Chem (2012) 55, 343-345. DOI 10.1007/s13765-012-2004-x.
Yong-Jin Kim et al., "An Experimental Study on Brain Damage and Cardiovascular System Effects of Angelicae Gigantis Radix Extract", J Korean Oriental Med 2000; 21(4) : 37-46.
Yong Yook Lee et al., "Platelet Anti-Aggregatory Effects of Coumarins from the Roots of Angelica genuflexa and A. gigas", Arch Pharm Res, vol. 26, No. 9, 723-726, 2003.
Lee, K. Y. et al., "Biological Activities of Extract from Aerial Parts of Angelica gigas Nakai", Journal of Agricultural, Life and Environmental Sciences vol. 27, No. 1, Mar. 2015.
Epo, Search Report of EP 19803580.0 dated May 31, 2022.

* cited by examiner

*Primary Examiner* — Qiuwen Mi
(74) *Attorney, Agent, or Firm* — Lex IP Meister, PLLC

(57) ABSTRACT

Provided are an antithrombotic composition (platelet aggregation inhibitor) comprising an *Angelica gigas* Nakai extract and a pharmaceutical composition for prevention and/or treatment of vascular disease, which comprises an *Angelica gigas* Nakai extract. The compositions are characterized in that they do not cause a gastrointestinal disorder.

4 Claims, 6 Drawing Sheets

[FIG. 1a]
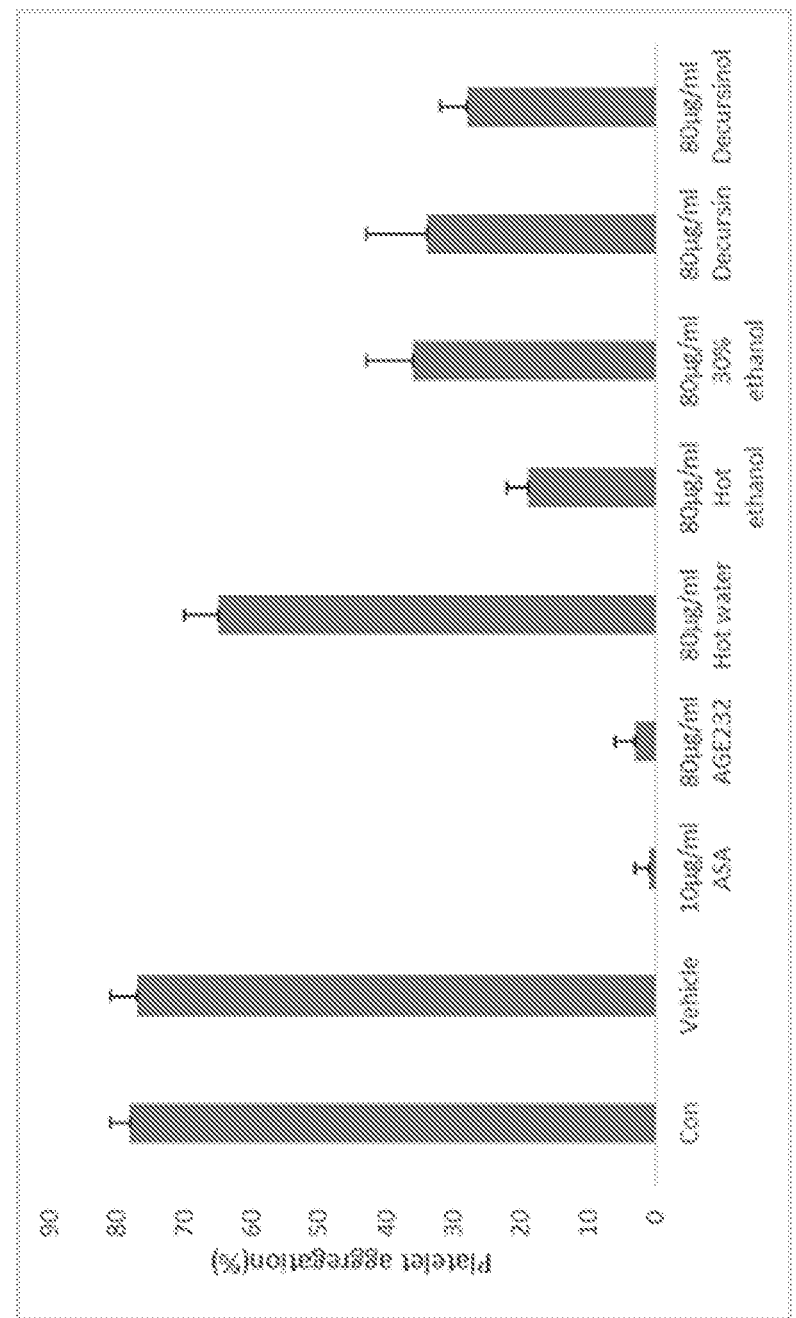

[FIG. 1b]
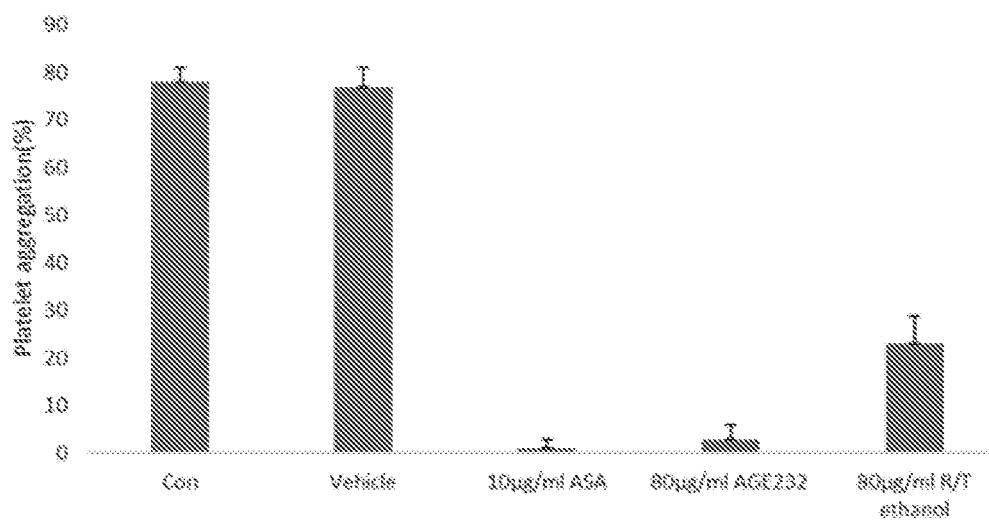

[FIG. 2]
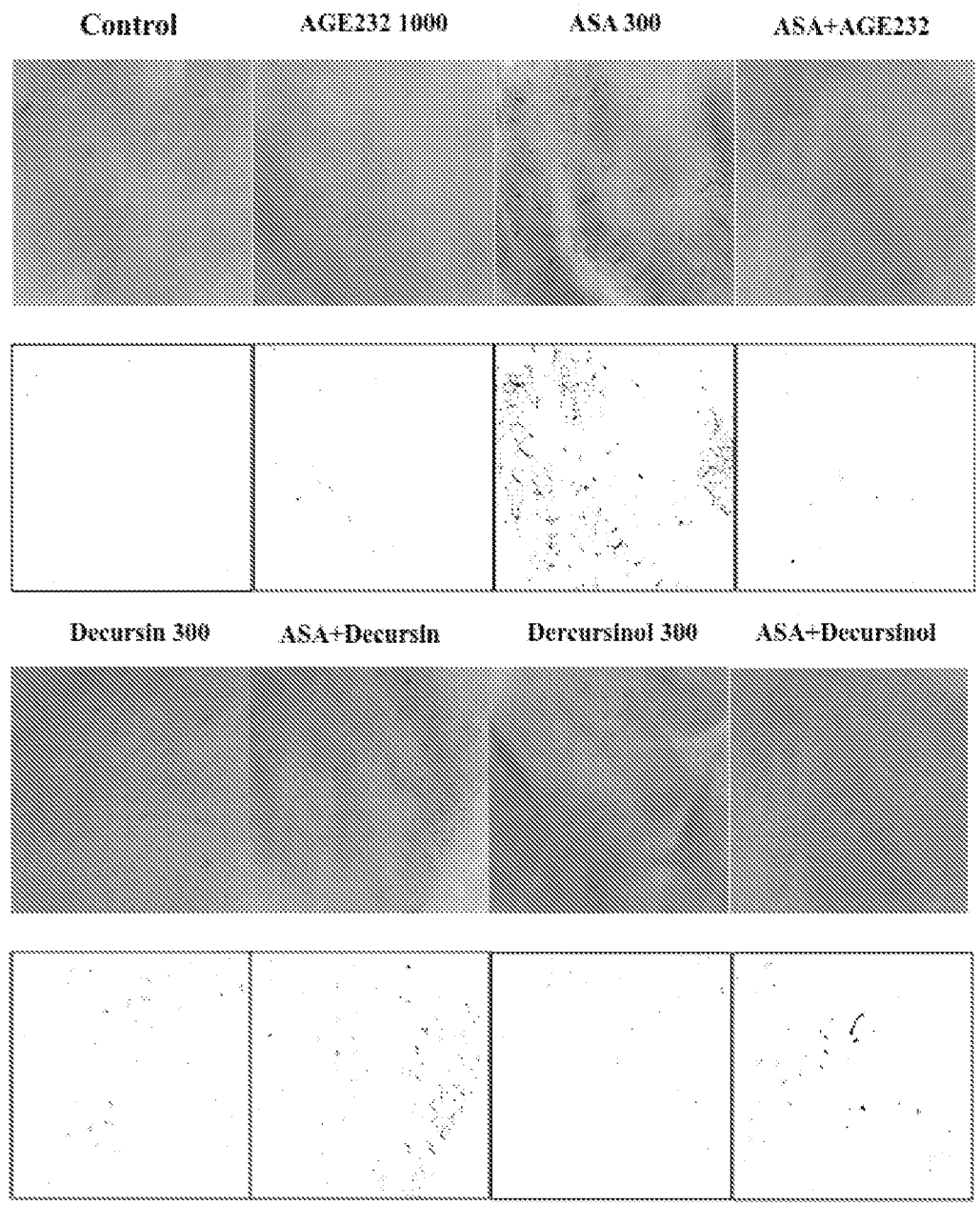

[FIG. 3]
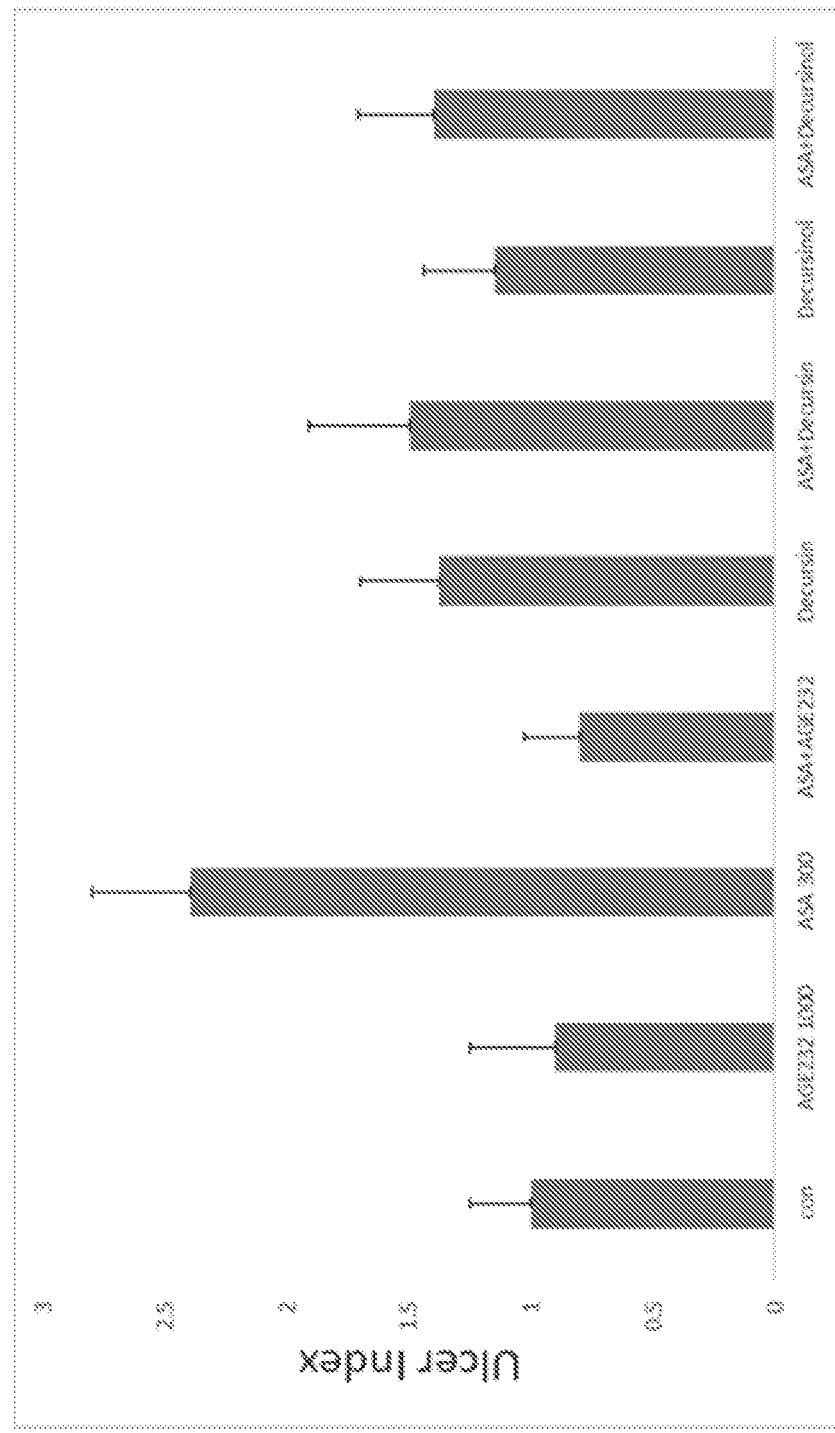

[FIG. 4]
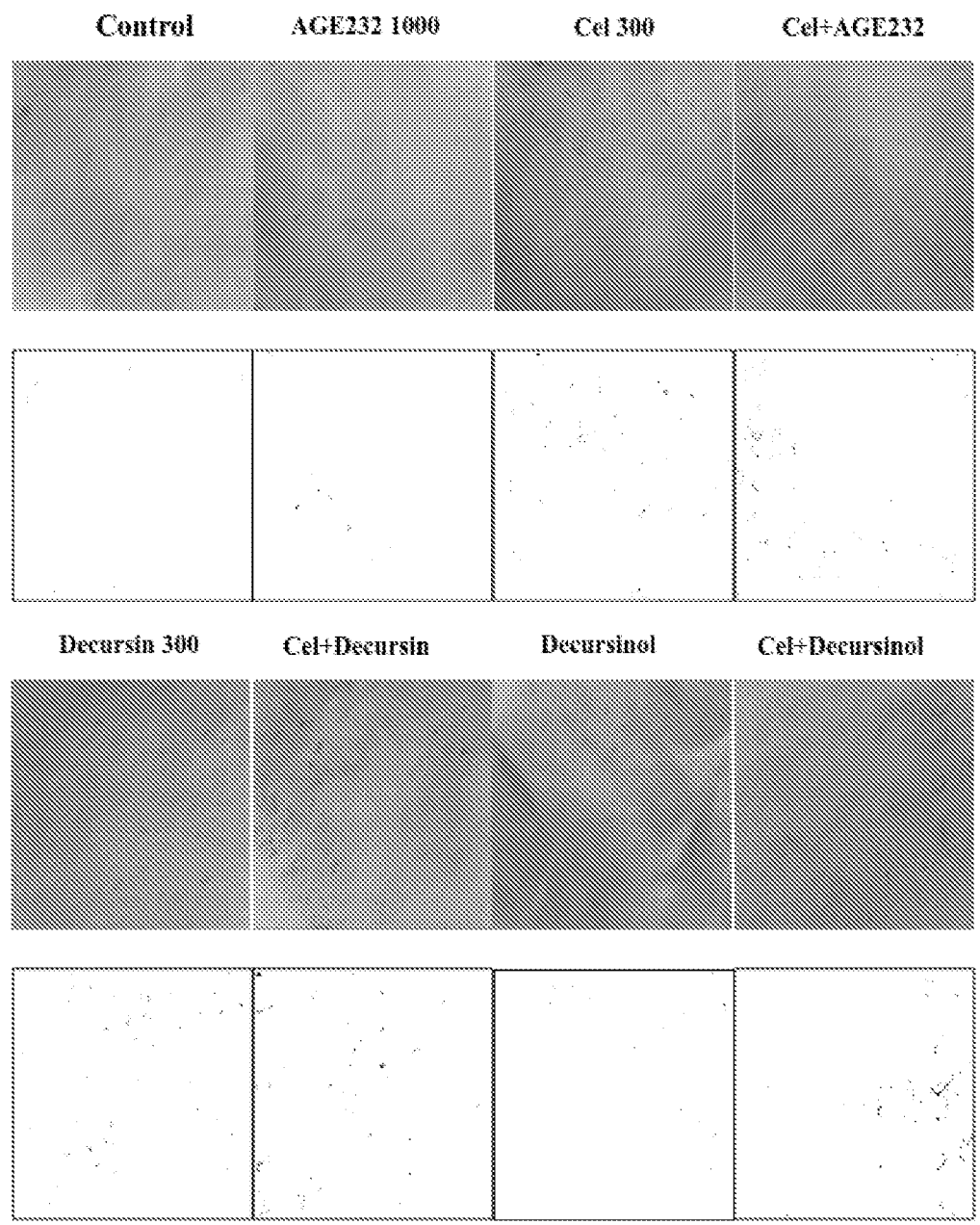

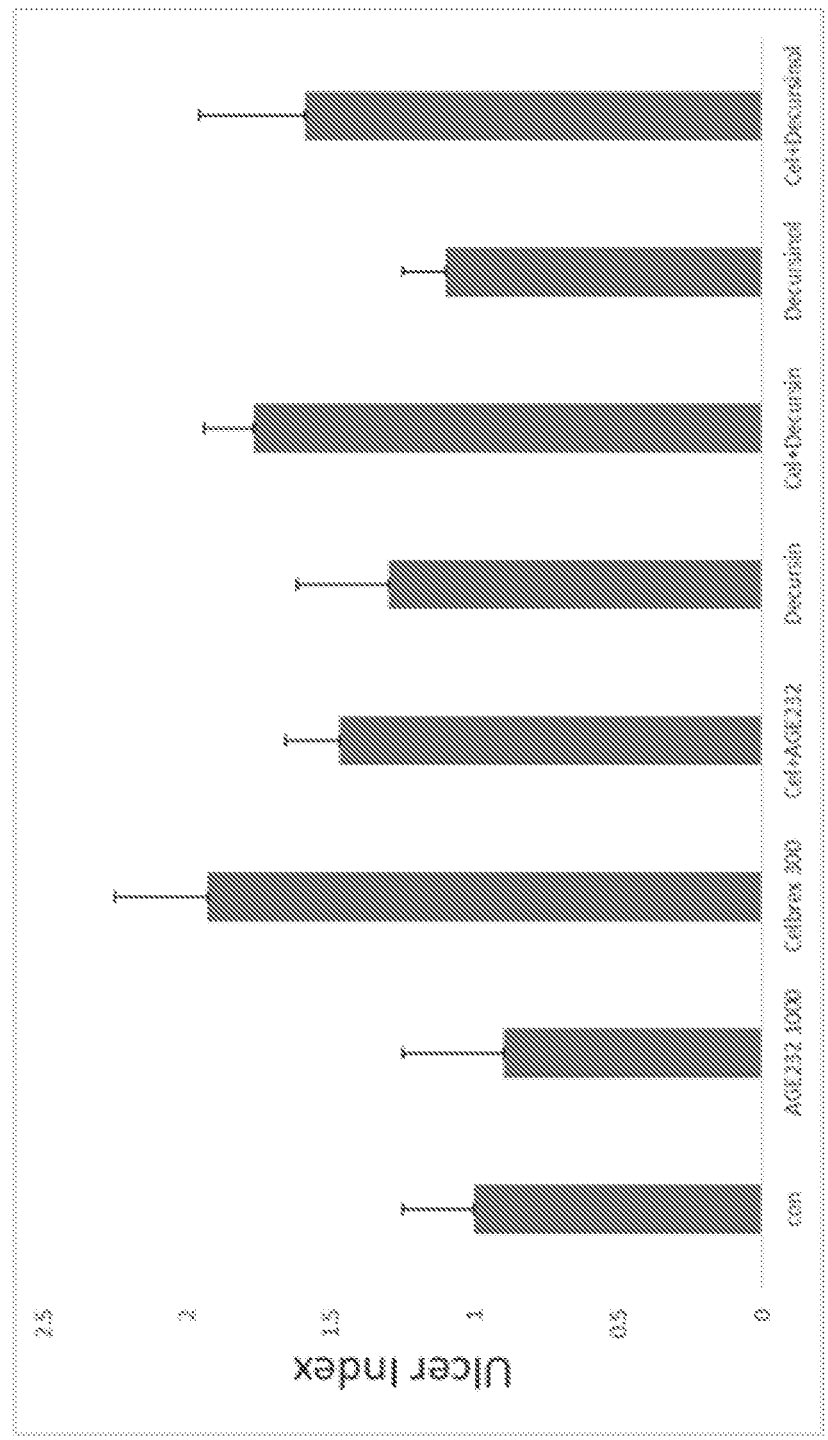
[FIG. 5]

ANTITHROMBOTIC COMPOSITION COMPRISING *ANGELICA GIGAS* NAKAI EXTRACT

TECHNICAL FIELD

The present disclosure provides an antithrombotic composition (platelet aggregation inhibitor) and a pharmaceutical composition for the prevention and/or treatment of a vascular disease, comprising an *Angelica gigas* Nakai extract. The composition can be characterized in that it does not cause a gastrointestinal disorder.

BACKGROUND ART

Vascular diseases refer collectively to all diseases caused by blockage or bursting of blood vessels, and includes cerebrovascular disease, cardiovascular disease (coronary artery disease), arteriosclerosis, peripheral vascular disease, etc. Vascular diseases are mainly brought about by thrombus caused by cholesterol, and the like, and a therapeutic effect can be obtained by inhibiting the aggregation of platelets. Previously, non-steroidal anti-inflammatory drugs (NSAIDs) such as aspirin and ibuprofen have been used to inhibit platelet aggregation.

Since aspirin (acetylsalicylic acid (ASA)) is a salicylate drug, which has antipyretic, analgesic, and anti-inflammatory effects, and has an inhibitory effect on platelet aggregation by inhibiting the production of prothrombin, it is also used to inhibit a secondary onset such as stroke. However, non-steroidal anti-inflammatory drugs such as aspirin can cause side effects such as gastric ulcers, and have side effects that can, especially, induce excessive bleeding in the stomach to cause gastrointestinal disorders.

Therefore, there is a need to develop a drug which inhibits platelet aggregation and/or has an excellent preventive or therapeutic effect on vascular diseases without causing gastrointestinal disorders.

DISCLOSURE

Technical Problem

One embodiment provides an antithrombotic pharmaceutical composition or a pharmaceutical composition for inhibiting platelet aggregation which comprises an *Angelica gigas* Nakai extract as an active ingredient.

Another embodiment t provides a pharmaceutical composition for the prevention and/or treatment of a vascular disease which comprises an *Angelica gigas* Nakai extract as an active ingredient.

Another embodiment provides an antithrombotic health functional food or a health functional food for inhibiting platelet aggregation which comprises an *Angelica gigas* Nakai extract.

Another embodiment provides a health functional food for the prevention and/or amelioration of a vascular disease which comprises an *Angelica gigas* Nakai extract.

Another embodiment provides a method of antithrombotic treatment (inhibiting platelet aggregation, or inhibition thrombus) which comprises administering a pharmaceutically effective amount of an *Angelica gigas* Nakai extract to a patient in need of the inhibition of platelet aggregation. The method may further comprise identifying a patient in need of platelet aggregation inhibition prior to the administering step.

Yet another embodiment provides a method of preventing and/or treating a vascular disease comprising administering a pharmaceutically effective amount of an *Angelica gigas* Nakai extract to a patient in need of prevention and/or treatment of a vascular disease. The method may further comprise identifying a patient in need of the prevention and/or treatment of a vascular disease prior to the administering step.

Yet another embodiment is based on the fact that the *Angelica gigas* Nakai extract does not cause a gastrointestinal disorder which is a side effect of conventional antithrombotic and/or vascular disease therapeutic agents, and provides the use of prophylactic, alleviating, ameliorating, mitigating, and/or therapeutic agents for a gastrointestinal disorder induced by conventional antithrombotic and/or vascular disease therapeutic agents, such as *Angelica gigas* Nakai extract, nonsteroidal anti-inflammatory drugs (NSAIDs).

Specifically, one embodiment provides a pharmaceutical composition for the prevention and/or treatment of a gastrointestinal disorder which comprises an *Angelica gigas* Nakai extract as an active ingredient. Another embodiment provides a health functional food for the prevention and/or amelioration of a gastrointestinal disorder which comprises an *Angelica gigas* Nakai extract. Another embodiment provides a method for preventing and/or treating a gastrointestinal disorder comprising administering a pharmaceutically effective amount of an *Angelica gigas* Nakai extract to a patient in need of the prevention and/or treatment of a gastrointestinal disorder. The method may further comprise a step of identifying the patient in need of the prevention and/or treatment of a gastrointestinal disorder, prior to the administering step. The gastrointestinal disorder may be gastric ulcer or gastric bleeding induced by antithrombotic and/or vascular disease therapeutic agents, for example, non-steroidal anti-inflammatory drugs (NSAIDs).

The other embodiment provides a pharmaceutical composition for the combined administration for anti-inflammation, analgesic, or prevention and/or treatment of an inflammatory disease, comprising an *Angelica gigas* Nakai extract and a non-steroidal anti-inflammatory drug. The other embodiment provides a method of anti-inflammation, analgesic, or prevention and/or treatment of an inflammatory disease which comprises administrating a combination of an *Angelica gigas* Nakai extract and a non-steroidal anti-inflammatory drug to a patient in need of anti-inflammation, analgesic, or prevention and/or treatment of an inflammatory disease. The combined administration step may be performed by administering an *Angelica gigas* Nakai extract and a non-steroidal anti-inflammatory drug simultaneously or sequentially, in any order. The method may further comprise identifying a patient in need of anti-inflammation, analgesic, or prevention and/or treatment of an inflammatory disease, prior to the combined administration step. The composition and method are characterized by being able to prevent, alleviate, ameliorate, mitigate, eliminate, or treat a gastrointestinal disorder such as gastric ulcer, gastric bleeding, etc. induced by a non-steroidal anti-inflammatory drug.

In addition, based on the antithrombotic and/or vascular disease therapeutic effects and the effect of not causing a gastrointestinal disorder, without causing any gastrointestinal disorders of *Angelica gigas* Nakai extract, provided herein is an application that can be used as an alternative to a portion or all of the antithrombotic and/or vascular disease therapeutic agents of the *Angelica gigas* Nakai extract.

Specifically, one embodiment provides a pharmaceutical composition for the combined administration for antithrombotic (or platelet aggregation inhibition) or for preventing and/or treating a vascular disease, comprising an *Angelica gigas* Nakai extract and an antithrombotic agent.

A further embodiment provides a method for antithrombotic treatment (or platelet aggregation inhibition or thrombus inhibition), or a method of preventing and/or treating a vascular disease, the method comprising co-administering an *Angelica gigas* Nakai extract and an antithrombotic agent to a patient in need of antithrombotic (or platelet aggregation inhibition) or the prevention and/or treatment of a vascular disease. The co-administration step may be performed by administering an *Angelica gigas* Nakai extract and a non-steroidal anti-inflammatory drug simultaneously or sequentially, in any order. The method may further comprise identifying a patient in need of the inhibition of platelet aggregation prior to the combined administration step.

Technical Solution

The present disclosure is associated with the antithrombotic, and prevention, treatment and/or amelioration effect of *Angelica gigas* Nakai extract.

More specifically, one embodiment provides an antithrombotic pharmaceutical composition (antithrombotic agent) or a pharmaceutical composition for inhibiting platelet aggregation (platelet aggregation inhibitor) which comprises an *Angelica gigas* Nakai extract as an active ingredient.

Another embodiment provides a pharmaceutical composition for the prevention and/or treatment of a vascular disease which comprises an *Angelica gigas* Nakai extract as an active ingredient.

Another embodiment provides an antithrombotic health functional food or a health functional food for inhibiting platelet aggregation which comprises an *Angelica gigas* Nakai extract.

Another embodiment provides a health functional food for the prevention and/or amelioration of a vascular disease which comprises an *Angelica gigas* Nakai extract.

Another embodiment provides a method of antithrombotic treatment (platelet aggregation inhibition, or thrombus inhibition) which comprises administering a pharmaceutically effective amount of an *Angelica gigas* Nakai extract to a patient in need of the inhibition of platelet aggregation. The method may further comprise identifying a patient in need of inhibition of platelet aggregation prior to the administering step.

Yet another embodiment provides a method of preventing and/or treating a vascular disease comprising administering a pharmaceutically effective amount of an *Angelica gigas* Nakai extract to a patient in need of prevention and/or treatment of a vascular disease. The method may further comprise identifying a patient in need of the prevention and/or treatment of a vascular disease prior to the administering step.

Yet another embodiment is based on the fact that the *Angelica gigas* Nakai extract does not cause a gastrointestinal disorder which is a side effect of conventional antithrombotic and/or vascular disease therapeutic agents, and provides the use of prophylactic, alleviating, ameliorating, mitigating, and/or therapeutic agents for a gastrointestinal disorder induced by conventional antithrombotic and/or vascular disease therapeutic agents, such as *Angelica gigas* Nakai extract, nonsteroidal anti-inflammatory drugs (NSAIDs).

Specifically, one embodiment provides a pharmaceutical composition for the prevention and/or treatment of a gastrointestinal disorder which comprises an *Angelica gigas* Nakai extract as an active ingredient. Another embodiment provides a health functional food for the prevention and/or amelioration of a gastrointestinal disorder which comprises an *Angelica gigas* Nakai extract. Another embodiment provides a method for preventing and/or treating a gastrointestinal disorder which comprises administering a pharmaceutically effective amount of an *Angelica gigas* Nakai extract to a patient in need of the prevention and/or treatment of the gastrointestinal disorder. The method may further comprise a step of identifying the patient in need of the prevention and/or treatment of the gastrointestinal disorder, prior to the administering step. The gastrointestinal disorder may be gastric ulcer or gastric bleeding induced by antithrombotic and/or vascular disease therapeutic agents, for example, non-steroidal anti-inflammatory drugs (NSAIDs).

The other embodiment provides a pharmaceutical composition for the combined administration for anti-inflammation, analgesic, or prevention and/or treatment of an inflammatory disease, comprising an *Angelica gigas* Nakai extract and a non-steroidal anti-inflammatory drug. The other embodiment provides a method of preventing and/or treating anti-inflammatory or analgesic, or inflammatory diseases which comprises administering a combination of an *Angelica gigas* Nakai extract and a non-steroidal anti-inflammatory drug to a patient in need of anti-inflammation, analgesic, or prevention and/or treatment of an inflammatory disease. The combined administration step may be performed by administering an *Angelica gigas* Nakai extract and a non-steroidal anti-inflammatory drug simultaneously or sequentially, regardless of the sequence. The method may further comprise identifying a patient in need of anti-inflammation, analgesic, or prevention and/or treatment of an inflammatory disease, prior to the combined administration step. The composition and method are characterized by being able to prevent, alleviate, ameliorate, mitigate, eliminate, or treat a gastrointestinal disorder such as gastric ulcer, gastric bleeding, etc. induced by a non-steroidal anti-inflammatory drug.

The content ratio of the *Angelica gigas* Nakai extract and the non-steroidal anti-inflammatory drug contained in the pharmaceutical composition for the combined administration or administered in the combined administration step may be appropriately prescribed according to the condition of a patient to be administered. For example, the ratio may be 1:0.1 to 10, 1:0.1 to 7.5, 1:0.1 to 5, 1:0.1 to 2.5, 1:0.1 to 1, 1:0.1 to 0.75, 1:0.1 to 0.5, 1:0.1 to 0.25, 1:0.25 to 10, 1:0.25 to 7.5, 1:0.25 to 5, 1:0.25 to 2.5, 1:0.25 to 1, 1:0.25 to 0.75, 1:0.25 to 0.5, 1:0.5 to 10, 1:0.5 to 7.5, 1:0.5 to 5, 1:0.5 to 2.5, 1:0.5 to 1, 1:0.5 to 0.75, 1:0.75 to 10, 1:0.75 to 7.5, 1:0.75 to 5, 1:0.75 to 2.5, 1:0.75 to 1, 1:1 to 10, 1:1 to 7.5, 1:1 to 5, 1:1 to 2.5, 1:2.5 to 10, 1:2.5 to 7.5, 1:2.5 to 5, 1:5 to 10, or 1:5 to 7.5 on a weight basis (weight of *Angelica gigas* Nakai extract: weight of non-steroidal anti-inflammatory drug), but is not limited thereto.

In addition, based on the antithrombotic and/or a vascular disease therapeutic effects and the effect of not causing a gastrointestinal disorder, without causing any gastrointestinal disorder of *Angelica gigas* Nakai extract, provided therein is an application that can be used as an alternative to a portion or all of the therapeutic agents for antithrombotic and/or a vascular disease of the *Angelica gigas* Nakai extract.

Specifically, a further embodiment provides a pharmaceutical composition for a combined administration for anti-thrombotic (or platelet aggregation inhibition) or for preventing and/or treating a vascular disease which comprises an *Angelica gigas* Nakai extract and an antithrombotic agent.

A further embodiment provides a method for antithrombotic treatment (or platelet aggregation inhibition or thrombus inhibition), or a method of preventing and/or treating a vascular disease, the method comprising co-administering an *Angelica gigas* Nakai extract and an antithrombotic agent to a patient in need of antithrombotic (or platelet aggregation inhibition), or the prevention and/or treatment of a vascular disease. The co-administration step may be performed by administering an *Angelica gigas* Nakai extract and a non-steroidal anti-inflammatory drug simultaneously or sequentially, in any order. The method may further comprise identifying a patient in need of the inhibition of platelet aggregation prior to the combined administration step.

The content ratio of the *Angelica gigas* Nakai extract and the non-steroidal anti-inflammatory drug contained in the pharmaceutical composition for the combined administration or administered in the combined administration step may be appropriately prescribed according to the condition of the patient to be administered. For example, the ratio may be 1:0.1 to 10, 1:0.1 to 7.5, 1:0.1 to 5, 1:0.1 to 2.5, 1:0.1 to 1, 1:0.1 to 0.75, 1:0.1 to 0.5, 1:0.1 to 0.25, 1:0.25 to 10, 1:0.25 to 7.5, 1:0.25 to 5, 1:0.25 to 2.5, 1:0.25 to 1, 1:0.25 to 0.75, 1:0.25 to 0.5, 1:0.5 to 10, 1:0.5 to 7.5, 1:0.5 to 5, 1:0.5 to 2.5, 1:0.5 to 1, 1:0.5 to 0.75, 1:0.75 to 10, 1:0.75 to 7.5, 1:0.75 to 5, 1:0.75 to 2.5, 1:0.75 to 1, 1:1 to 10, 1:1 to 7.5, 1:1 to 5, 1:1 to 2.5, 1:2.5 to 10, 1:2.5 to 7.5, 1:2.5 to 5, 1:5 to 10, or 1:5 to 7.5 on a weight basis (weight of *Angelica gigas* Nakai extract: weight of non-steroidal anti-inflammatory drug), but is not limited thereto.

As used herein, the "antithrombotic agent" can be selected among all drugs (small molecule compounds, proteins, peptides, natural products, natural extracts, etc.) that have antithrombotic (e.g., platelet aggregation inhibition) effects, and it may be, for example, one or more selected from non-steroidal anti-inflammatory drugs (NSAIDs) including aspirin, ibuprofen, and the like, but is not limited thereto.

As used herein, the 'non-steroidal anti-inflammatory drug(s)' or the 'non-steroidal anti-inflammatory drug(s)' may be one or more selected from the group consisting of aspirin, celecoxib, ibuprofen, and the like.

As used herein, the 'treatment' is used in a sense that includes mitigation, alleviation, recovery, or amelioration of symptoms, reduction of the range of diseases, delay or alleviation of the progression of the disease, amelioration, alleviation or stabilization of disease states or symptoms, partial or complete recovery, prolongation of survival, other beneficial treatment results, and the like.

As used herein, the 'antithrombotic agent' refers to any pharmaceutical composition that acts to inhibit the formation of thrombus in blood vessels, and/or to prevent, alleviate, ameliorate, and/or treat symptoms brought about by thrombus, and can be expressed as a platelet aggregation (coagulation) inhibitor, an antiplatelet agent, an antithrombosis agent, and the like.

As used herein, the 'vascular disease' refers to any disease brought about by thrombus in blood vessels, and may be one or more selected from the group consisting of cerebrovascular diseases such as stroke, cerebral infarction, or hypertension, cardiovascular diseases such as myocardial infarction or angina, arteriosclerosis, peripheral vascular diseases, and the like.

The antithrombotic agents and compositions for preventing or treating a vascular disease provided in the present disclosure have the advantage of not inducing a gastrointestinal disorder such as gastric ulcer or gastrointestinal bleeding which are side effects of non-steroidal anti-inflammatory drugs (NSAIDs) such as aspirin and ibuprofen used as conventional antithrombotic agents.

As used herein, the 'inflammation' is meant to include any inflammation caused by infection of bacteria, fungi, viruses, parasites, and/or foreign immunogenic substances (e.g., proteins, small molecule compounds, etc.), or autoimmunity. As used herein, the 'anti-inflammation' may refer to an action of preventing, alleviating, recovering, ameliorating, or eliminating (treating) inflammation.

As use herein, the 'pain' may be selected from neuropathic pain (neuralgia, etc.), headache, muscle pain, stomach pain, menstrual pain, etc., the 'analgesia' may mean mitigation, amelioration, recovery, or elimination (treatment) of pain.

As used herein, the 'inflammatory disease' may be selected from arthritis (e.g., osteoarthritis, rheumatoid arthritis, etc.), pericarditis, vasculitis (Kawasaki disease), myelitis, etc., but is not limited thereto.

*Angelica* is a perennial herbaceous plant belonging to the umbel family, and is cultivated mainly for medicinal purposes in Korea, Japan, and China. *Angelica* is divided into *Angelica gigas* Nakai produced in Korea, *Angelica acutiloba* Kitagaw produced in Japan, and *Angelica sinensis* Diels produced in China. It is known that their ingredients and pharmacological effects are different. Since ancient times, *Angelica* has used young sprouts as herbs, and the root is used as a medicine for various diseases such as analgesia, anticancer, reduction of renal toxicity, improvement of liver function, treatment of diabetic hypertension The *Angelica gigas* Nakai extract may be obtained by extracting *Angelica gigas* Nakai (e.g., whole or root) with one or more extraction solvents selected from the group consisting of water and a linear or branched alcohol having 1 to 4 carbon atoms. In one embodiment, the *Angelica gigas* Nakai extract may be a *Angelica gigas* Nakai ethanol aqueous solution extract obtained by extracting the *Angelica gigas* Nakai (e.g., root) with 30 to 100% (v/v), 40 to 100% (v/v), 50 to 100% (v/v), 60 to 100% (v/v), 70 to 100% (v/v), 80 to 100% (v/v), 90 to 100% (v/v), 92 to 100% (v/v), 96 to 100% (v/v), or 98 to 100% (v/v) ethanol aqueous solution (e.g., 98% (v/v) aqueous ethanol solution (alcohol)). Further, the *Angelica gigas* Nakai extract may be extracted at 10 to 90° C., 10 to 80° C., 10 to 70° C., 10 to 60° C., 10 to 50° C., 20 to 90° C., 20 to 80° C., 20 to 70° C., 20 to 60° C., 20 to 50° C., 30 to 90° C., 30 to 80° C., 30 to 70° C., 30 to 60° C., 30 to 50° C., 40 to 90° C., 40 to 80° C., 40 to 70° C., 40 to 60° C., 40 to 55° C., or 40 to 50° C.

*Angelica gigas* Nakai extract used herein, such as *Angelica gigas* Nakai ethanol extract (extracted with 90 to 100% (v/v), 92 to 100% (v/v), 96 to 100% (v/v), or 98 to 100% (v/v) ethanol aqueous solution at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., 40 to 55° C., or 40 to 50° C.) may be those in which, per 100 g, (1) the content of decursin may be about 2000 mg or more, about 2200 mg or more, about 2400 mg or more, about 2600 mg or more, or about 2800 mg or more, about 3000 mg or more, for example, 2000 to 5000 mg, 2000 to 4500 mg, 2000 to 4000 mg, 2000 to 3500 mg, 2200 to 5000 mg, 2200 to 4500 mg, 2200 to 4000 mg, 2200 to 3500 mg, 2400 to 5000 mg, 2400 to 4500 mg, 2400 to 4000 mg, 2400 to 3500 mg, 2600 to 5000 mg, 2600 to 4500 mg, 2600 to 4000 mg, 2600 to 3500 mg, 2800 to 5000 mg, 2800 to 4500 mg, 2800 to 4000 mg, 2800 to 3500 mg, 3000 to 5000 mg, 3000 to 4500 mg, 3000 to 4000 mg, or 3000 to 3500 mg, and/or (2) the content of decursinol angelate may be about 1200 mg or more, about 1400 mg or more, about 1600 mg or more, or about 1800 mg or more, for example, 1200 to 3000 mg, 1200 to 2800 mg, 1200 to 2600 mg, 1200 to 2400 mg, 1200 to 2200 mg, 1400 to 3000 mg, 1400 to 2800 mg, 1400 to 2600 mg, 1400 to 2400 mg, 1400 to 2200 mg, 1600 to 3000 mg, 1600 to 2800 mg, 1600 to 2600 mg, 1600 to 2400 mg, 1600 to 2200 mg, 1800 to 3000 mg, 1800 to 2800 mg, 1800 to 2600 mg, 1800 to 2400 mg, or 1800 to 2200 mg, and/or (3) the content of Nodakenin may be about 800 mg or more, about 1000 mg or more, about 1200 mg or more, about 1500 mg or more, about 1700 mg or more, about 2000 mg or more, about 2200 mg or more, about 2500 mg or more, or about 2700 or more, for example, 800 to 5000 mg, 800 to 4500 mg, 800 to 4000 mg, 800 to 3500 mg, 800 to 3200 mg, 1000 to 5000 mg, 1000 to 4500 mg, 1000 to 4000 mg, 1000 to 3500 mg, 1000 to 3200 mg, 1200 to 5000 mg, 1200 to 4500 mg, 1200 to 4000 mg, 1200 to 3500 mg, 1200 to 3200 mg, 1500 to 5000 mg, 1500 to 4500 mg, 1500 to 4000 mg, 1500 to 3500 mg, 1500 to 3200 mg, 1700 to 5000 mg, 1700 to 4500 mg, 1700 to 4000 mg, 1700 to 3500 mg, 1700 to 3200 mg, 2000 to 5000 mg, 2000 to 4500 mg, 2000 to 4000 mg, 2000 to 3500 mg, 2000 to 3200 mg, 2200 to 5000 mg, 2200 to 4500 mg, 2200 to 4000 mg, 2200 to 3500 mg, 2200 to 3200 mg, 2500 to 5000 mg, 2500 to 4500 mg, 2500 to 4000 mg, 2500 to 3500 mg, 2500 to 3200 mg, 2700 to 5000 mg, 2700 to 4500 mg, 2700 to 4000 mg, 2700 to 3500 mg, or 2700 to 3200 mg, and/or (4) the content of beta-sitosterol may be 30 mg or more, 50 mg or more, 100 mg or more, 150 mg or more, 200 mg or more, 250 mg or more, or 300 mg or more, for example, 30 to 1000 mg, 30 to 800 mg, 30 to 600 mg, 30 to 500 mg, 30 to 400 mg, 50 to 1000 mg, 50 to 800 mg, 50 to 600 mg, 50 to 500 mg, 50 to 400 mg, 100 to 1000 mg, 100 to 800 mg, 100 to 600 mg, 100 to 500 mg, 100 to 400 mg, 150 to 1000 mg, 150 to 800 mg, 150 to 600 mg, 150 to 500 mg, 150 to 400 mg, 200 to 1000 mg, 200 to 800 mg, 200 to 600 mg, 200 to 500 mg, 200 to 400 mg, 250 to 1000 mg, 250 to 800 mg, 250 to 600 mg, 250 to 500 mg, 250 to 400 mg, 300 to 1000 mg, 300 to 800 mg, 300 to 600 mg, 300 to 500 mg, or 300 to 400 mg.

The *Angelica gigas* Nakai extract contained as an active ingredient in the pharmaceutical composition may be in the form of a dried product, a concentrated product, or a concentrated dried product.

The content of the *Angelica gigas* Nakai extract contained as an active ingredient in the pharmaceutical composition can be appropriately adjusted according to the form and purpose of use, the condition of the patient, the type and severity of symptoms, and the like, and may be 0.001 to 99.9% by weight, 0.01 to 70% by weight, or 0.1 to 50% by weight based on the solid content weight, but is not limited thereto. The solid content weight refers to the weight of the solids from which the solvent ingredient has been removed from the extract, as described above.

The pharmaceutical composition may be administered to mammals, comprising humans, dogs, cats, horses, cows, pigs, goats, rabbits, mice, rats, etc., or cells or tissues isolated therefrom, or cultures thereof via various routes. The mode of administration may be any mode commonly used in the art, and may be, for example, oral administration, or parenteral administration such as intravenous administration, intramuscular administration, subcutaneous administration, intraperitoneal administration, and local administration of the lesion site (e.g., joint). The pharmaceutical composition may be used after being formulated into an oral preparation, such as powders, granules, tablets, capsules, suspensions, emulsions, syrups, and aerosols, etc., and a parental preparation, such as epidermal formulations, suppositories, or sterile injection solutions, in accordance with a conventional method.

The pharmaceutical composition may further contain pharmaceutically suitable and physiologically acceptable adjuvants such as carriers, excipients and diluents, etc. in addition to the *Angelica gigas* Nakai extract. Examples of the carriers, excipients and diluents may comprise lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinyl pyrrolidone, water, methyl hydroxybenzoate, propyl hydroxybenzoate, talc, magnesium stearate, and mineral oil. When formulated into a preparation, one or more diluting agents or excipients selected from the group consisting of commonly-used fillers, weighting agents, binding agents, wetting agents, disintegrating agents, and surfactants can be used. Solid preparations for oral administration comprise tablets, pills, powders, granules, capsules, syrups, powdered drugs, and suspensions, and the like, and these solid preparations may be prepared by mixing the extract with at least one excipient, for example, at least one selected from the group consisting of starch, calcium carbonate, sucrose, lactose, gelatin, and the like. In addition to the simple excipient, a lubricant such as magnesium stearate and talc are also used. Liquid preparations for oral administration comprise at least one selected from the group consisting of a suspension, a liquid for internal use, an emulsion, a syrup, etc. In addition to a commonly used simple diluent such as water and liquid paraffin, various excipients, for example, at least one selected from the group consisting of a humectant, a sweetener, an aromatic, a preservative, etc. may also be contained. Formulations for parenteral administration comprise a sterilized aqueous solution, a non-aqueous solution, a suspension, an emulsion, a lyophilized formulation and a suppository, transdermal formulations, etc. The non-aqueous solution or suspension may contain at least one selected from the group consisting of propylene glycol, polyethylene glycol, a vegetable oil such as olive oil, an injectable ester such as ethyl oleate, etc.

The pharmaceutical composition may be administered in a pharmaceutically effective amount. A dose of the pharmaceutical composition may be prescribed depending on various factors such as formulation method, administration mode, the patient's age, weight, sex, pathological condition, diet, the time of administration, administration interval, the route of administration, the rate of excretion, and reaction sensitivity. The dose may vary depending on the patient's age, weight, sex, administration mode, health condition, and the severity of diseases. It may be administered once a day or in several divided doses at fixed time intervals according to the decision of a doctor or pharmacist. For example, the daily dose may be in the rage of 0.001 to 1000 mg/kg, specifically 0.01 to 100 mg/kg, more specifically 0.1 to 20 mg/kg, based on the solid content weight of the active ingredient (*Angelica gigas* Nakai extract), but is not limited thereto. The daily dose may be formulated as one formulation into a unit dose form or distributed into separate dose forms, or may be comprised within a multiple dose package. The above doses illustrate an average case and can be high or low depending on individual differences.

Another embodiment of the present disclosure provides a method for preparing an antithrombotic agent or a composition having an effect of preventing, treating and/or ameliorating a vascular disease, comprising preparing an *Angelica gigas* Nakai extract.

The step of preparing an *Angelica gigas* Nakai extract may comprise a step of extracting *Angelica gigas* Nakai with at least one selected from the group consisting of 1 to 10 times volume, 2 to 8 times volume, or 4 to 6 times volume of water and a linear or branched alcohol having 1 to 4 carbon atoms (e.g., ethanol), for example, 90 to 100% (v/v), 92 to 100% (v/v), 96 to 100% (v/v), or 98 to 100% (v/v) ethanol aqueous solution (e.g., 98% (v/v) ethanol aqueous solution (alcohol)) at 10 to 80° C., 10 to 70° C., 10 to 60° C., 10 to 50° C., 20 to 80° C., 20 to 70° C., 20 to 60° C., 20 to 50° C., 30 to 80° C., 30 to 70° C., 30 to 60° C., 30 to 50° C., 40 to 80° C., 40 to 70° C., 40 to 60° C., 40 to 55° C., or 40 to 50° C. The extraction time is satisfactory as long as the extraction can be performed sufficiently, and may set to the level of 1 hour or more, 2 hours or more, 3 hours or more, or 4 hours or more, for example, 1 to 12 hours, 2 to 12 hours, 3 to 12 hours, 4 to 12 hours, 1 to 6 hours, 2 to 6 hours, 3 to 6 hours, or 4 to 6 hours, but is not limited thereto.

The extraction process used in the above method can be performed by any commonly used extraction method, and it may be performed, for example, by one or more methods selected from the group consisting of hot water extraction, ultrasonic extraction, reflux extraction, and the like, but is not limited thereto.

In another embodiment, the present disclosure provides a health functional food for antithrombotic (for inhibiting platelet aggregation) or for the prevention and/or amelioration of a vascular disease, comprising an *Angelica gigas* Nakai extract.

The health functional foods are foods produced using raw materials and ingredients (hereinafter, "functional raw materials") having nutrients that are liable to be deficient in daily meals, and functions that are useful to the human body, and means all foods that help to maintain health or prevent and/or ameliorate certain diseases or symptoms, and the form of the final product is not particularly limited. For example, the health functional food may be selected from the group consisting of various foods, beverage compositions, and food additives, but is not limited thereto.

The content of *Angelica gigas* Nakai extract contained in the health functional food is appropriately determined according to the form of the food, the desired use, and the like, and is not particularly limited. For example, the content may be 0.001 to 95% by weight or 0.01 to 90% by weight of the total food weight.

The health functional foods may further comprise at least one selected from the group consisting of various nutrients, vitamins, minerals (electrolytes), flavoring agents such as synthetic flavors or natural flavors, colorants, enhancers (cheese, chocolate, etc.), pectic acid or salts thereof, alginic acid or salts thereof, organic acids, protective colloidal thickeners, pH regulators, stabilizers, preservatives, glycerin, alcohols, carbonating agents used in carbonated beverages, etc. In addition, the health functional food, in particular, the health functional beverage composition may contain fruit pulp for the production of natural fruit juice, fruit juice beverage, or vegetable beverage. These ingredients can be used independently or in combination. The ratio of these additives is generally selected from the range of 0.001 to about 20 parts by weight per 100 parts by weight of the total health functional food, but is not limited thereto.

Advantageous Effects

As confirmed herein, since the *Angelica gigas* Nakai extract exhibits excellent antithrombotic effects without inducing a gastrointestinal disorder, it can be usefully applied as an antithrombotic agent or a therapeutic agent for vascular disease.

BRIEF DESCRIPTION OF THE DRAWINGS

FIGS. 1a and 1b are graphs showing the antithrombotic effect of the *Angelica gigas* Nakai extract in human blood.

FIG. 2 is a photograph showing the appearance of the gastric mucosa when the *Angelica gigas* Nakai extract was administered in a mouse model in which gastrointestinal disorders are induced by aspirin.

FIG. 3 is a graph quantitatively showing the degree of the damage to the gastric mucosa identified in FIG. 2 (Ulcer index; UI).

FIG. 4 is a photograph showing the appearance of the gastric mucosa after administration of the *Angelica gigas* Nakai extract in a mouse model in which gastrointestinal disorders were induced by Celebrex.

FIG. 5 is a graph quantitatively showing the degree of the damage to the gastric mucosa identified in FIG. 4 (Ulcer index; UI).

MODE FOR INVENTION

Hereinafter, the present disclosure will be described in detail by way of examples, but these are for illustrative purposes only and are not intended to limit the scope of the present disclosure. It will be obvious to those skilled in the art that the examples described below may be modified without departing from the scope of the essential gist of the invention.

Example 1: Preparation of *Angelica gigas* Nakai Extract 1.1. Preparation of *Angelica gigas* Nakai Ethanol Extract

*Angelica gigas* Nakai roots were washed with clean water and dried sufficiently. The dried *Angelica gigas* Nakai roots were crushed, 5 volume times (500 ml) of ethanol (98% (v/v) ethanol (alcohol)) was added to 100 g of the obtained powder, extracted at 40 to 60° C. for 4 hours or more, and then filtered through a 1 um (micrometer) filter, and the filtrate was heated and concentrated until it became 10% of the original weight. Crystalline cellulose was gradually added to the obtained concentrate, continuously concentrated, dried completely, and then powdered to prepare an *Angelica gigas* Nakai ethanol extract powder (hereinafter, referred to as AGE232).

1.2. Preparation of *Angelica gigas* Nakai Ethanol High-Temperature Extract

*Angelica gigas* Nakai roots were washed with clean water and dried sufficiently. The dried *Angelica gigas* Nakai roots were crushed, 5 volume times (500 ml) of ethanol (98% (v/v) ethanol (alcohol)) was added to 100 g of the obtained powder, extracted at about 90° C. for 4 hours or more, and then filtered through a 1 um (micrometer) filter, and the filtrate was heated and concentrated until it became 10% of the original weight. Crystalline cellulose was gradually added to the obtained concentrate, continuously concentrated, dried completely, and then powdered to prepare a high-temperature *Angelica gigas* Nakai ethanol extract powder.

1.3. Preparation of *Angelica gigas* Nakai Ethanol (Low-Concentration) Extract

*Angelica gigas* Nakai roots were washed with clean water and dried sufficiently. The dried *Angelica gigas* Nakai roots were crushed, 5 volume times (500 ml) of 30% (v/v) ethanol was added to 100 g of the obtained powder, extracted at 40 to 60° C. for 4 hours or more, and then filtered through a 1 um (micrometer) filter, and the filtrate was heated and concentrated until it became 10% of the original weight. Crystalline cellulose was gradually added to the obtained concentrate, continuously concentrated, dried completely, and then powdered to prepare an ethanol (low-concentration) *Angelica gigas* Nakai extract.

1.4. Preparation of *Angelica gigas* Nakai Hot Water Extract 5,000 ml of distilled water was added to 2 kg of *Angelica gigas* Nakai, extracted 4 times for each 8 hours in a water bath (about 90° C.), filtered and the solvent was evaporated with a concentration device to obtain a herbal extract. The obtained extract was freeze-dried for 12 hours in a freeze dryer, and then powdered to prepare a dried powdered *Angelica gigas* Nakai hot water extract powder.

1.5. Preparation of *Angelica gigas* Nakai Ethanol R/T (Room Temperature) Extract

*Angelica gigas* Nakai roots were washed with clean water and dried sufficiently. The dried *Angelica gigas* Nakai roots were crushed, 5 volume times (500 ml) of ethanol (98% (v/v) ethanol (alcohol)) was added to 100 g of the obtained powder, extracted at room temperature (about 25° C.) for 4 hours or more, and then filtered through a 1 um (micrometer) filter, and the filtrate was heated and concentrated until it became 10% of the original weight. Crystalline cellulose was gradually added to the obtained concentrate, continuously concentrated, dried completely, and then powdered to prepare a high-temperature *Angelica gigas* Nakai ethanol R/T extract powder.

Example 2: Antithrombotic Effect Test 2.1. Ex-Vivo Test

To prepare platelets, human platelet-rich plasma (PRP) was obtained from the Red Cross Blood Center (Seoul, Korea) (PRP concentration: $1 \times 10^9$ platelets/ml).

Platelet analysis was performed as follows:

An aggregometer (Instrument: Whole blood/optical Lumi-Aggregometer Model 700 (CHRONO-LOG)) manufactured by Chrono-Log Co. was used as an analytical instrument. The light transmission value of PPP (Platelet Poor Plasma; Red Cross Blood Center (Seoul, Korea)) was used as the baseline value, and the maximum value interfering with light transmission due to PRP (Platelet Rich Plasma) aggregation was converted into a percentage (%). Collagen (12.5 µg/ml) was used as an aggregation agent.

The inhibitory effect of each extract on platelet aggregation was measured using a dual channel aggregometer. Platelet-rich plasma (PRP) and platelet-poor plasma (PPP) were used. 360 µl of the prepared PRP was put into a cuvette, and 40 µl of 0.25% (w/v) PEG200 (vehicle), aspirin (10 ug/ml), or each extract (80 ug/ml) was added thereto. For comparison, instead of the above extract, aspirin (10 ug/ml), which is well known as an antithrombotic agent, or decursin (80 ug/ml; single compound) or decursinol (80 ug/ml; single compound), which is an active ingredient of the *Angelica gigas* Nakai extract, were used to perform the same experiment.

The mixture was cultured with stirring at 1000 rpm and 37° C. in an aggregometer for 2 minutes. After culturing, 12.5 µg/ml of collagen was added to induce platelet aggregation, and after 6 minutes, changes in light transmission were confirmed, and the degree of platelet aggregation was measured. The obtained platelet aggregation (%) is shown in FIGS. 1a and 1b (con: non-administration group). As shown in FIGS. 1a and 1b, the *Angelica gigas* Nakai extract, in particular, the extract using ethanol as an extraction solvent showed a lower platelet aggregation rate compared to the vehicle-administered group and the control group (non-administered group). In particular, it can be confirmed that the *Angelica gigas* Nakai extract (AGE232) had remarkably low platelet aggregation, as compared with the extracts of other extraction conditions (type of extraction solvent, concentration of extraction solvent, and/or extraction temperature), and not only it showed a platelet aggregation equal to that of aspirin (ASA) used as an antithrombotic agent, but also showed remarkably low platelet aggregation than decursin and decursinol which are the single compounds. These effects show that *Angelica gigas* Nakai extract, especially ethanol extract (e.g., AGE232) not only has an excellent antithrombotic effect, but also has an antithrombotic effect equivalent to that of aspirin (ASA) used as a conventional antithrombotic agent, and has a remarkably higher antithrombotic effect than decursin and decursinol which are the single compounds.

2.2. In-Vivo Test

Preparation of Experimental Animals

As for the experimental animals, 5-week-old female ICR mice provided by YoungBio were stabilized in an animal laboratory at a temperature of 24±1° C., a humidity of 55±5% in a 12-hour day-night cycle for 1 week and used in the experiments.

The change in behavioral capacity was evaluated for the prepared thrombus-induced mouse model using Rota-rod, and the antithrombotic effect of the *Angelica gigas* Nakai extract was evaluated. The thrombus-induced mouse model was prepared as follows. A 6-week-old ICR mouse (about 20 to 25 g) stabilized as an experimental mouse was prepared, and subjected to Rota-rod training, and the reference value was created three times, and the rotation speed was set to 24 rpm, and objects withstanding without falling at a rotation speed of 300 or more were selected. The selected mice were divided into treatment groups, and after administration of each drug (see Table 1), after 90 minutes, collagen (13.2 µg) and epinephrine (114 µg) were mixed and injected into the tail vein to induce thrombus. After 15 minutes, Rota-rod testing was repeated 3 times (rotation speed: 24 rpm), and the difference in athletic performance was analyzed by the following Equation:

Protection rate (%)=[(Total number of individuals−Number of killed or paralyzed individuals)/Total number of individuals]×100

(Number of total individuals: the number of individuals that did not fall at a rotation speed of 300 or more at a rotation speed of 24 rpm in Rota-rod testing;

Number of killed or paralyzed individuals: The number of individuals who fell at a rotation speed of 24 rpm or less in Rota-rod testing at a rotation speed of 150 or less)

The obtained protection rate is shown in Table 1 below:

TABLE 1

| Group | Dose | Number of killed or paralyzed individuals / Number of total individuals | Protection (%) |
|---|---|---|---|
| Control | PEG 25% (w/v) | 15/18 | 16.7 |
| ASA (Aspirin) | 100 mg/kg | 11/20 | 45 |

TABLE 1-continued

| Group | Dose | Number of killed or paralyzed individuals / Number of total individuals | Protection (%) |
|---|---|---|---|
| AGE232 | 10 mg/kg | 10/19 | 47.3 |
| Decursin | 10 mg/kg | 11/18 | 38.9 |
| Decursinol | 10 mg/kg | 12/19 | 36.8 |
| Hot water extract | 10 mg/kg | 15/19 | 21.1 |
| Ethanol high-temperature extract | 10 mg/kg | 12/18 | 33.4 |
| 30% ethanol extract | 10 mg/kg | 13/20 | 35 |
| Ethanol R/T extract | 10 mg/kg | 11/18 | 38.9 |

As shown in Table 1, *Angelica gigas* Nakai extract showed excellent protection rate compared to the control group. In particular, the *Angelica gigas* Nakai extract ethanol extract (AGE232) not only showed remarkably superior protection rate compared to the extract under other extraction conditions, but also exhibited protection rates equal to or higher than those of aspirin used as a conventional antithrombotic agent, and decursin and decursinol which are single compounds.

Example 3. Gastrointestinal Disorder Inhibition Testing (In-Vivo)

Experimental Animals

Male ICR mice, 5 per cage, room temperature (22±0.5° C.), bred under the conditions of a 12-hour day-night cycle.

Water and food were fed without limitation, the animals were adapted to the experiment at least 2 hours before experiment, and to reduce the variation, proceeded in a light phase (10:00-17:00), The test drug was orally administered for each treatment group once daily for 5 days using syringes as follows (ASA (Aspirin) and Celebrex were used to induce gastrointestinal disorders):

Treatment of Experimental Animal

ASA 300 or Cel 300: Aspirin™ (ASA, Bayer AG) 300 mg/kg or Celebrex™ (Cel, Pfizer) 300 mg/kg, administered for 5 consecutive days;

Con: control;

AGE232 1000: *Angelica gigas* Nakai extract AGE232 1000 mg/kg, administered for 5 consecutive days;

ASA+AGE232 or Cel+AGE232:

ASA+AGE232 or Cel+AGE232: combined administration of *Angelica gigas* Nakai extract AGE232 1000 mg/kg and Aspirin™ (ASA) 300 mg/kg or Celeblex™ (Cel) 300 mg/kg, administered for 5 consecutive days;

Decursin 300: decursin 300 mg/kg, administered for 5 consecutive days;

ASA+Decursin or Cel+Decursin: combined administration of dercursin 300 mg/kg and Aspirin™ (ASA) 300 mg/kg or Celebrex™ (Cel) 300 mg/kg, administrated for 5 consecutive days;

Decursinol 300: decursinol 300 mg/kg, administered for 5 consecutive days;

ASA+Decursinol or Cel+Decursinol: combined administration of dercursinol 300 mg/kg and Aspirin™ (ASA) 300 mg/kg or Celebrex™ (Cel) 300 mg/kg, administrated for 5 consecutive days.

Dissection and Observation of Gastric Mucosa

Immediately after dislocation of the cervical spine, the stomach was taken out, opened along the greater curvature, and developed on a cork plate. The inner surface was rinsed with iced cold saline, blood and the like were wiped off, the inner wall of the stomach was observed using a high-resolution microscope, etc. The results are shown in FIG. 2 (aspirin-administered gastrointestinal disorder-inducing group) and FIG. 4 (Celebrex-administered gastrointestinal disorder-inducing group).

For the quantitative measurement of stomach injury, the gastric mucosal morbidity rate (Ulcer index (UI)) was measured by the following method:

(I) Viscous bleeding and erosions site <1 mm: gastric mucosal edema, hyperemia, presence of one bleeding;

(II) Erosion site 1~3 mm: When small mucosal bleeding was accompanied by small gastric mucosal erosion;

(III) Erosion site >3 mm: A bleeding edge was accompanied by severe erosion, erosive injuries or ulcers are present.

Ulcer index (UI): $(1*n*(I))+(2*n*(II))+(3*n*(III))$/number of animals (n is Means the number of animals corresponding to the standard of I, II, and III)

The Ulcer index (UI) obtained for the results of FIGS. 2 and 4 using the above method was shown in FIG. 3 (aspirin (ASA)-administered gastrointestinal disorder-inducing group) and FIG. 5 (celecoxib (cel)-administered gastrointestinal disorder-inducing group), respectively.

As shown in FIGS. 2 to 5, (1) when comparing the results of ASA 300 or Cel 300 and ASA+AGE232 or Cel+AGE232, the gastrointestinal disorders (gastric bleeding) induced by aspirin or celebrex were significantly reduced when administered together with *Angelica gigas* Nakai extract, and (2) when aspirin or celebrex was administered in combination with *Angelica gigas* Nakai extract, the gastrointestinal disorders (gastric bleeding) induced by aspirin or celebrex were significantly reduced as compared with the combined administration of decursin and decursinol which are single compounds.

Example 4. Analysis of Active Ingredients Between Each Extract (HPLC)

<Preparation of Sample Solution>

1 g of 5 types of samples (*Angelica gigas* Nakai water extract, *Angelica gigas* Nakai ethanol high temperature extract, *Angelica gigas* Nakai 30% ethanol extract, *Angelica gigas* Nakai ethanol extract (AGE232), or *Angelica gigas* Nakai R/T extract) were exactly taken and put in a 50 ml volumetric flask, and then dissolved by adding about 30 ml of methanol (100%), filled with methanol to a marked line, filtered, and used as a sample solution. The sample solution was prepared by varying the degree of dilution according to the type of sample and analysis items.

<Preparation of Standard Solution>

10 mg of decursinol standard product (purity 98% or more), 5 mg of decursinol standard product (purity 98% or more), and 5 mg of decursinol angelate standard product (purity 98% or more) were taken and put in a 25 ml flask, and dissolved by adding 100% methanol, filled with methanol to a marked line, filtered, and used as a sample solution. A standard solution having a concentration of 12.5-25-50-100-200 µg/ml was prepared from this standard solution and used for measuring the calibration curve.

<HPLC Operating Conditions>

Testing was performed with the sample solution and standard solution according to the operating conditions of the liquid chromatography below to calculate the content of decursinol, and decursinol angelate:

Column: Cadenza CW C18, (150*4.6 mm, 3 μm) or equivalent column;

Detector: Ultraviolet spectrophotometer (detection wavelength: 330 nm);

Flow rate: 0.7 ml/min;

Mobile phase: Water (A %), Acetonitrile (B %), 0-5 min (20, B), 5-6 min (20→40, B), 6-22 min (40→55, B), 22-23 min (55→80, B), 23-25 min (80, B), 25-27 min (20, B); Sample injection amount: 10 μl.

<Result>

The ingredient analysis results of each of the obtained extracts are shown in Table 2 below.

TABLE 2

Analysis results of major ingredients according to the extraction solvent and extraction method of *Angelica gigas* Nakai

| Extraction Method | | Water (hot water) extract | Ethanol high-temperature extract (90° C.) | 30% ethanol extract | Ethanol extract (AGE 232) | Ethanol R/T extract |
|---|---|---|---|---|---|---|
| Ext. vol. before concent. (ml) | | 1,800 | 650 | 1210 | 465 | 401 |
| Ext. weight after concent. (g) | | 42.0 | 24.2 | 21.7 | 30.5 | 25.1 |
| Total extracted compounds from 100 g dried *Angelica* | Decursin (mg) | 19 | 1640 | 1101 | 3243 | 1570 |
| | Decursinol angelate (mg) | 10 | 790 | 865 | 1995 | 811 |
| | Nodakenin (mg) | 559 | 1332 | 543 | 2982 | 792 |
| *gigas* Nakai (mg) | β-Sitosterol (mg) | 13 | 85 | 35 | 324 | 255 |

As shown in Table 2, it was confirmed that the *Angelica gigas* Nakai extract had a relatively high content (on weight base) of active ingredients such as decursin, decursinol angelate, nodakenin, and beta-sitosterol, in particular, the content of the active ingredient of *Angelica gigas* Nakai ethanol extract (AGE232) was remarkably high.

The invention claimed is:

1. A method of antithrombotic treatment comprising administering a pharmaceutically effective amount of an *Angelica gigas* Nakai extract to a patient in need of inhibition of platelet aggregation,
    wherein the *Angelica gigas* Nakai extract is an *Angelica gigas* Nakai ethanol extract obtained by extracting *Angelica gigas* Nakai with 90 to 100% (v/v) ethanol solution at 40 to 80° C.

2. The method of antithrombotic treatment according to claim 1, wherein the *Angelica gigas* Nakai extract is an *Angelica gigas* Nakai ethanol extract obtained by extracting *Angelica gigas* Nakai with 90 to 100% (v/v) ethanol solution at 40 to 60° C.

3. The method of antithrombotic treatment according to claim 2, wherein the ethanol solution has a concentration of 96 to 100% (v/v).

4. The method of antithrombotic treatment according to claim 1, which does not cause a gastrointestinal disorder.

* * * * *